United States Patent [19]

Graham et al.

[11] 4,325,973
[45] Apr. 20, 1982

[54] HYDROXYALKYL AMIDES AS FUNGICIDES TO EUMYCOTINA IN PHANEROGAMIA PLANT LIFE

[75] Inventors: David E. Graham, Westfield, N.J.; Joseph P. Copes, deceased, late of Easton, Pa., by Anna M. Copes, legal representative

[73] Assignee: GAF Corporation, New York, N.Y.

[21] Appl. No.: 170,446

[22] Filed: Jul. 21, 1980

Related U.S. Application Data

[63] Continuation of Ser. No. 758,585, Jan. 12, 1977, abandoned.

[51] Int. Cl.³ ............................................ A01N 37/18
[52] U.S. Cl. ................................... 424/320; 424/311; 424/324
[58] Field of Search .............................. 424/320, 324

[56] References Cited

U.S. PATENT DOCUMENTS

| | | | |
|---|---|---|---|
| 2,166,119 | 7/1939 | Bousquet | 424/320 |
| 2,419,888 | 4/1947 | Nolan et al. | 424/304 |
| 2,426,885 | 9/1947 | Kilgore | 424/320 |
| 2,484,296 | 10/1949 | Kilgore et al. | 424/320 |
| 2,504,427 | 4/1950 | Kilgore | 424/320 |
| 2,504,477 | 4/1950 | Weber et al. | 424/320 |
| 2,520,551 | 8/1950 | Kilgore | 424/320 |
| 2,936,323 | 5/1960 | Eden | 424/324 |
| 3,193,451 | 7/1965 | Reinisch | 424/320 |
| 3,228,832 | 1/1966 | Margot et al. | 424/320 |

*Primary Examiner*—Leonard Schenkman
*Attorney, Agent, or Firm*—James Magee, Jr.; Marilyn J. Maue

[57] ABSTRACT

This invention relates to the control and/or eradication of Eumycotina type fungi is phanerogamia plants with one or more of the substituted carboxylic amides having the formula:

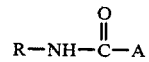

wherein A is an organic radical of from 2 to 14 carbon atoms and is selected from the group consisting of hydroxyalkyl, hydroxyalkoxy, haloalkyl radicals and substituted alkylether radicals having the structure $-R_1-O-R_2-$, where $R_1$ is alkylene of from 1 to 6 carbon atoms and $R_2$ is alkyl of from 1 to 6 carbon atoms substituted with a hydroxy, carboxylate or halocarboxylate group; and wherein R is an acyclic alkyl radical, an alkenyl radical having one or more doubly bonded carbon atoms, a mono- or di- fluorinated benzyl radical or a mono- or di- chlorinated benzyl radical, said R radical containing from 4 to 20 carbon atoms. The invention also relates to a method of using a fungicidal amount of said carboxylic acid amide or carboxylic amide mixtures on phanerogamia plants for control or eradication of Eumycotina infection.

10 Claims, No Drawings

HYDROXYALKYL AMIDES AS FUNGICIDES TO EUMYCOTINA IN PHANEROGAMIA PLANT LIFE

This is a continuation of application Ser. No. 758,585, filed Jan. 12, 1977, now abandoned.

The present carboxylic acid amides provide significantly improved control of Eumycotina type fungus which attacks plant crops and additionally prevent renewed attacks of said fungus on treated plants. In many cases, the present fungicides provide complete eradication of fungus infection and in other cases result in a 20% improvement over fungicides presently in commercial use. The prolonged protection against fungus attack achieved by the present carboxylic amides is attributed to their systemic action in entering the plant tissues.

Since the present fungicides contain no substituents which are known to be toxic to humans or animals and leave no residue in plant tissues which could be expected to lead to such toxicity, the present compounds offer an ecologically acceptable agent for control for fungus infection. A further advantage from the standpoint of ecology is the biodegradable nature of the present fungicides which prevents pollution of streams and drinking water often resulting from spray applications of other fungicides, such as the thio compounds. The systemic action causes the present fungicides to reach all portions of the plant, including the lower leaves, stem, roots, flower head and underleaf where fungi tend to grow most abundantly. Thirdly, the present fungicidal protectants, which are sparingly soluble in water, are not easily removed nor are their effects diluted by rain, watering or other aqueous plant sprays and thus can be used in combination with growth regulating and fertilizing agents. The present fungicides also possess thermal stability over the range of normal growing temperatures, 32°-120° F.

The organic commercial fungicides employed heretofore are, for the most part, sulfur or phosphorous-containing compounds which are specific to certain fungi and which are not biodegradable. For example, sodium 4-(dimethylamino) phenyl diazene sulfonate (Dexon) is useful in controlling water molds, but has little effect on many higher fungi. Dithiocarbamates in the form of ferric, zinc, sodium and manganous salts have enjoyed wide popularity as fungicides; however, close control on application rates is necessary, since these chemicals are known to adversely effect cell metabolism in plants when dosage exceeds certain levels. Accordingly, these metal salts can be phytotoxic so that arrest of the fungi infection may be accompanied by destruction of the plant. In contrast the present fungicidal compounds control a wide range of fungi, including smuts, molds, rusts, cankers and slimes, and are nontoxic to plants, humans and animals. Thus, they are also useful as post harvest fungicides on vegetables and as a general fungus protectant for plants and seeds. Finally, the predominantly aliphatic character of the present fungicidal compounds has the advantage of being fungistatic and more readily utilized by plant tissue.

Other systemic fungicides which have been recently introduced, such as thiazolylbenzimidazole, and butyl-carbamoyl-benzimidazole carbamic acid and the oxathiins have limited effectiveness, being used mainly to control smuts (Ustilaginales) and are expensive to produce. In contrast, compounds of the present invention can be easily prepared by processes generally known in the art, e.g., by the reaction between primary aliphatic amines and lactones under mild conditions of temperature and pressure.

Accordingly, it is an object of the present invention to provide an economical fungicide having efficacy for a broad range of fungi of the pathogenic Eumycotina type which are completely nontoxic with respect to plants and animals and which provides protection against fungi infection over a prolonged period so as to extend protection through the entire growing season of a plant.

Another object of the present invention is to provide a biodegradable fungicide which avoids build-up in the soil and harboring of bacterial growth.

Another object of this invention is to provide a fungicide which is effective at low dosage rates and is nontoxic to plants an animals.

Still another object of this invention is to provide a systemic fungicide with aliphatic character which possesses high solubility in a broad range of conventional and inexpensive commercial solvents and which is economical to produce.

These and other objects and advantages will become apparent from the following descriptions and disclosure.

According to the present invention, control of Eumycotina fungi in phanerogamia plants is achieved by applying a fungicidal amount of one or more substituted carboxylic amides having the formula:

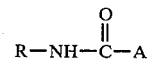

wherein A is an organic radical having from 2 to 14 carbon atoms and is selected from the group consisting of hydroxyalkyl, hydroxyalkoxy, haloalkyl radicals and substituted alkylether radicals having the structure —R$_1$—O—R$_2$—, where R$_1$ is alkylene of from 1 to 6 carbon atoms and R$_2$ is alkyl of from 1 to 6 carbon atoms substituted with a hydroxy, carboxylate or halocarboxylate group; and wherein R is an acyclic alkyl radical, an alkenyl radical having one or more doubly bonded carbon atoms, a mono- or di-fluorinated benzyl radical or a mono- or di-chlorinated benzyl radical, said R radical containing from 4 to 20 carbon atoms.

Preferred of the above group of substituted carboxylic amides are those wherein R is a radical consisting of hydrogen and from 8 to 18 carbon atoms and A is hydroxy alkyl containing 2 to 4 carbon atoms. The fungicidal compounds of this group have superior and distinct advantages in that they display at least 10% higher activity than the remaining members of the group. Also, this preferred group of compounds is more economical to produce and is more readily accessible to plant tissue through the stoma or cuticle to provide systemic action. Additionally, only low dosages of this preferred group are required to control fungus infection. Most preferred of this group are those hydroxy butyramides having an alkyl or alkenyl group of 8 to 18 carbon atoms attached to the amido nitrogen.

The fungicides of the present invention are prepared by contacting a primary amine substituted with an alkyl or an alkenyl radical, having one or more doubly bonded carbon atoms or a halobenzyl radical and containing 4 to 20 carbon atoms in the molecule, and a lactone having 3 to 6 carbon atoms in the heterocylic lactone ring at a temperature of between about 30° C. to about 200° C., preferably from 50° C. to about 180° C. under a pressure of between about atmospheric and about 50 psig., preferably under atmospheric pressure, for a period of from about 30 minutes to about 5 hours. The mixing of the reactants may be accompanied by agitation and warming of the reactants, if desired. A mole ratio of amine to lactone between about 5:1 and about 1:5 can be employed in the reaction zone, although ratios as close to stoichiometry as convenient are preferred. When stoichiometric amounts of reactants are employed, the reactants is practically quantitative and the products are obtained in a state sufficiently pure for direct use in a fungicidal composition.

The products of this process are recovered as a liquid or a solid, depending on the molecular weight of the compound. Generally, the hydroxy butyramides containing a N-alkyl or a N-alkenyl group of 4 to 8 carbon atoms are liquids; whereas those containing a N-alkyl or a N-alkenyl group of 8 to 20 carbon atoms are solids. These products can be separated from the reaction mixture by extraction in a suitable inert liquid solvent, by precipitation and drying of the precipitate or by any other convenient and conventional means.

Suitable solvents which may be used to extract liquid products include alcohols of from one to five carbon atoms, hydrocarbon oils pyridine, acetone, methylethyl ketone, ethyl ketone, carbon tetrachloride, kerosene, naphtha, chloroform, mineral oil, a petroleum oil fraction or any other conventionally employed inert solvent in which the product is readily soluble. If desired, the product can be purified before use, e.g. by crystallization from a solvent or by one or more solvent extractions and evaporations. This procedure is particularly directed to the preparation of the preferred group of carboxylic amide fungicides as hereinabove defined.

The fungicides of the above formula were A is haloalkyl can be prepared by further reacting the hydroxy carboxylic acid amide product of the above procedure in a suitable inert solvent such as benzene, xylene, pyridine, etc., with a solution of thionyl halide at elevated temperature up to the reflux temperature of the mixture for a period of from about 0.5 to about 5 hours. The resultint N-alkyl halocarboxylic acid amide can be then filtered from solution and dried. The halocarboxylic amide fungicides of this invention include the fluoro-, chloro- and bromo-analogs.

The fungicides of the above formula where A represents a substituted alkyl ether radical containing a hydroxy radical can be prepared by further reacting the above N-alkyl hydroxycarboxylic acid amide product with a heterocyclic oxyalkane, e.g. oxirane, epoxybutane, epoxypentane, epoxyhexane, etc. This reaction is carried out at a temperature between about 100° C. and about 180° C. under superatmospheric pressure up to about 75 psig., or the autogeneous pressure developed in a closed system where the epoxyalkane is introduced as a compressed gas into the sealed reactor. The reaction is enhanced by the presence of a catalyst such as an alkali metal hydroxide and by agitation. Generally, the reaction is completed within a period of from about 0.5 to about 5 hours after which an N-alkyl hydroxyalkoxy carboxylic amide product is precipitated and dried.

A method for the preparation of fungicides wherein A is an alkyl ether radical and contains a carboxylate group or a halocarboxylate group comprises reacting the above N-alkyl hydroxyalkoxy carboxylic acid amide with a carboxylic anhydride in the presence of an alkali metal salt of the carboxylic acid or a halocarboxylic acid halide at a temperature of from about 20° C. to about 180° C. for a period of from 1 to about 20 hours. After completion of reaction, the mixture is conveniently drowned with water and product is recovered by salting out and phase separation. In the present invention, the fungicidal products wherein A is haloalkyl or an ether radical where $R_2$ is alkyl substituted with a hydroxy or a halocarboxylate group are novel compounds.

The fungicidal compounds of this invention are generally applied to phanerogamia plants at the rate of between about 0.5 pounds and 30 pounds per acre, preferably between 1 pound and about 10 pounds per acre. The fungicides are usually employed as aqueous solutions, suspensions, dispersions or emulsions. In the case of the N-lower alkyl carboxylic amides, the compounds are directly soluble in water so that aqueous solutions may be readily applied. In the case of N-alkyl having 10 or more carbon atoms, the compounds are only sparingly soluble in water; accordingly, aqueous suspensions, dispersions or emulsions of these higher molecular weight compounds comprise the fungicidal compositions. Emulsions, suspensions or dispersions of these higher molecular weight fungicides are prepared by dissolving the compound in a suitable carrier such as for example hydrocarbon oil, kerosene, naphtha, mineral oil, alcohol, or any other suitable solvents mentioned hereinbefore in which the fungicidal compound is soluble. The resulting solution is then mixed with water to provide a suitable emulsion. If desired, an emulsifying agent such as a fatty acid, a calcium, sodium or potassium salt of a fatty acid, a nonionic surfactant, a long-chain alcohol such as lauryl alcohol or a taurine, such as a steroyl taurine may be added to improve emulsification. The entire mixture is then shaken stirred or agitated in any other convenient manner until the liquid is homogeneous or uniformly emulsified or dispersed. It is to be understood that a nonaqueous solvent solution of the fungicide can also be employed.

The concentration of the fungicidal compound in the aqueous solution, suspension, dispersion, emulsion or nonaqueous solution varies between about 25 ppm and about 2,500 ppm, preferably between about 30 ppm and about 800 ppm based on total liquid composition.

Alternatively, the fungicidal compounds of the present invention may be applied as solids to the plant species, in which case the fungicide is mixed with or deposited on talc, mica, fuller's earth, diatomacious earth, bentonite, natural clays, pyrolite, powders of walnut shell, wheat, redwood, soya bean, cotton seed flower, etc., and any other solid conditioning agent or carrier of the kind conventionally employed in preparing fungicides in granular dust or powdered form. The concentration of the fungicide in the solid carrier is the same as stated above for the solution, suspension, dispersion or emulsion.

It is to be understood that mixtures of the above-named fungicides can comprise the fungicidal compositions and that other agents such as growth regulators, herbicides, fertilizer materials and insecticides can also be included in the final fungicidal compositions of the present invention, as well as other fungicides.

The phanerogamia plants to which the fungicidal composition is applied include the gymnosperms and angiosperms; species of which are exemplified by legumes such as peas, beans, tomatoes, lettuce, carrots, beets, potatoes, cucumber, etc.; graminae such as wheat, oats, rye, barley, rice, corn, tobacco, etc.; ornamentals such as roses, asters, tulips, hyacinths, daffodils, gladioli, zinnias, sweet peas, phlox, and tubers such as tuberous begonias, iris, etc., and trees, such as cedar, pines, spruces, juniper, walnut, hickery, redwood, oak, apple, cherry, peach, pear, plum, lemon, orange, etc.

Examples of the Eumycotina fungi inhibited by the present fungicidal compositions include Ascomycetes, Basidiomycetes, Deuteromycetes, and Phycomycetes. Illustrating the species of Ascomycetes are: Taphrina, Penicillium, Aspergillus, Ceratocystis, Meliola, Sphaerotheca, Erysiphe, Uncinula, Claviceps, Neurospora, Phyllachora, Hypoxylon, Gnomonia, Endothia, Glomerella, Nectria, Gibberella, Sclerotina, Elsinoe, Pleospora, Cochliobolus, Ophiobolus, Mycosphaerella, and Venturia. Species of Basidiomycetes include: Ustilago, Sphacoletheca, Tilletia, Urocystis, Puccina, Gymnosporangium, Uromyces, Thanatephorus, Stereum, Polyporus, Fomes, Lycoperdales, Phallales, and Nidulariales. Species of Deuteromycetes include: Graphium, Septoria, Diplodia, Colletotrichum, Verticillium, *Botrytis cinerea*, Helminthosporium, Alternaria, and Sclerotium. Species of Phycomycetes include: *Synchytrium endobioticum, Urophlyctis alfalfae, Olpidium brassicae, Aphanomyces cochlioides, Aphanomyces euteiches, Albuzo candida,* Pythium, Phytophthora, Sclerospora, Plasmopara, Bremia, Peronospora, Plasmodiophora, brassicae, *Spongospora subterranea, Rhizopus stolonifer* and Mucor spp.

In order that the invention may be better understood, reference is had to the following examples which are provided to illustrate the preferred embodiments for treatment of infected plant species. It is to be understood that any Eumycotina infected phanerogamia plant can be substituted in any of the following examples for control of infection and that any of the above-named fungicidal species can be substituted in any of the examples which employ a related species to provide similar arrest and control of fungi infection. Also, it is to be understood that any of the fungi falling within the above classes can be substituted for those named in the following examples and that these substituted fungi infections will be similarly arrested. Accordingly, such substitutions are included within the scope of this invention.

All proportions, parts and amounts in the following examples are by weight unless otherwise specified.

PREPARATION OF FUNGICIDES

Generally, the preparation of the present N-alkyl hydroxycarboxylic acid amide fungicides includes contacting amine and lactone, corresponding to the product moieties, in about stoichiometric amounts at a temperature preferably between about 80° C. and about 150° C. whereupon an exothermic reaction ensues. To minimize the formation of by-product, it has been found desirable to maintain the temperature at not more than about 160° C. Accordingly, the reaction mixture may be cooled so as to avoid exceeding such temperature levels.

In the following examples on the preparation of fungicides, the yield, physical character and solubility in alcohols such as methanol, ethanol and propanol and in ketone such as acetone were determined, after which the products were subjected to further analysis such as infrared (IR) or nuclear magnetic resonance spectra (NMR). Particular attention was given to the present monosubstituted amide configurations as characterized by the primary band of their respective carbonyl groups. This characteristic band is reported in the examples as the IR value in microns (mu). The carbonyl band for the monosubstituted amide in IR analysis is in the range of 6.0 to 6.17 microns.

EXAMPLE A

Preparation of N-butyl-4-hydroxybutyramide

Into a glass reaction vessel were introduced 73 grams of butylamine and 86 grams of γ-butyrolactone which reactants upon mixing, warmed to about 50° C. This liquid mixture was then heated to 100° C. on a steam bath and reaction was completed in 1.5 hours. The product, which was obtained in quantitative amount, i.e. greater than 95% conversion of butyrolactone, was then air-cooled to room temperature and the clear liquid product recovered. The product which is soluble in alcohols, dissolved in all proportions in methanol. Infrared analysis showed the characteristic band at 6.12 mu.

EXAMPLE B

Preparation of 4-hydroxy-N-octylbutyramide

In a glass reaction vessel, 129.25 grams of octylamine were mixed with 86.1 grams of butyrolactone, whereupon a rise in temperature was noted. The mixture was then heated to 100° C. on a steam bath until the reaction was completed in a period of 2 hours. A conversion of butyrolactone greater than 95% was obtained. The product, upon air cooling to room temperature formed a hard, white waxy solid. IR=6.10 mu. The product which is soluble in alcohols, was soluble in methanol in all proportions.

EXAMPLE C

Preparation of N-decyl-4-Hydroxybutyramide

In a glass reaction vessel, 157.3 grams of decylamine was mixed with 86.1 grams butyrolactone, whereupon the temperature rose to about 150° C. Reaction was spontaneous, and greater than 95% conversion of the butyrolactone to product was achieved. Titration of the product indicated that only 0.4 weight percent free amine remained unreacted. The liquid product was cooled by pouring on a glass surface at room temperature, whereupon the product froze to a hard white, waxy solid. Titration of the remaining reaction mixture indicated that only 0.4 weight percent free amine remained after removal of product. IR=6.11 mu.

EXAMPLE D

Preparation of N-dodecyl-4-hydroxybutyramide

In a glass reaction vessel, 185.4 grams of dodecylamine were mixed with 86.1 grams butyrolactone, whereupon a slight increase in temperature was noted. The mixture was then heated to 100° C. on a steam bath until reaction was completed in a period of 3 hours. The resulting liquid product was then poured onto a glass plate at room temperature, whereupon the product froze to a hard, white, waxy solid. Greater than 95% conversion of the butyrolactone was obtained. IR=6.10 mu.

EXAMPLE E

Preparation of 4-hydroxy-N-octadecylbutyramide

In a glass reaction vessel, 13.5 grams of octadecylamine were admixed with 4.3 grams of butyrolactone. The mixture was then heated to 150° C. by means of an oil bath until the reaction was complete in a period of 2 hours. A conversion of greater than 95% based on butyrolactone was achieved. Upon cooling to room temperature, the product formed a white to pale yellow, hard, waxy solid. Substantially all of the butyrolactone was reacted indicating greater than 95% conversion.

Other N-alkyl-substituted hydroxyalkylamides, such as the nonyl-, tridecyl-, tetradecyl-, pentadecyl-, hexadecyl-, heptadecyl-, nonadecyl-, ecosyl-, 4-ethylhexyl-, 4-ethyldecyl-, 4,6-dimethyldodecyl-, and 8-ethyloctadecyl-N-substituted hydroxybutyramides, -propionamides, -valeramides, -caproamides, -lauramides, -palmitamides, -stearamides, and -oleamides can be prepared according to the method of the above examples by substituting the corresponding amine and lactone or amide reactants.

EXAMPLE F

Preparation of 4-hydroxy-N-(9-octadecenyl)butyramide

Oleylamine derived from fat was titrated and found to have an equivalent weight of 266.9 grams (theory = 267.5 grams). In a glass reaction vessel, 266.9 grams of the oleylamine were admixed with 86.1 grams of butyrolactone and the mixture heated to 100° C. on a steam bath until reaction was completed in a period of 2 hours. Greater than 95% conversion of the butyrolactone was achieved. The product upon cooling to room temperature produced a slightly off-white, hard, waxy solid which was found to be readily soluble in alcohols. IR = 6.14 mu.

Other N-alkenyl and N-alkadienyl substituted hydroxyalkylamides, such as the 10-dodecenyl, 8-decenyl-, 4-hexadecenyl-, 4,8-dodecadienyl-, and 2-ethyl-6-octadecenyl-N-substituted hydroxybutyramides, -propionamides, -valeramides, -caproamides, -lauramides, -palmitamides, -stearamides, and -oleamides can be prepared by substituting the corresponding alkenylamine and corresponding lactone or amide reactant in this example.

EXAMPLE G

Preparation of N-(2-ethylhexyl)-4-hydroxybutyramide

In a glass reaction vessel 12.9 grams of 2-ethylhexylamine were admixed with 8.6 grams of butyrolactone and the mixture heated to 100° C. on a steam bath until reaction was completed in a period of one hour. A conversion of greater than 95%, based on butyrolactone, was achieved. The product upon cooling to room temperature was a colorless, clear, moderately viscous liquid. IR = 6.09 mu.

EXAMPLE H

Preparation of 4-chloro-N-dodecylbutyramide

In a glass reaction vessel, 20 grams (0.0738 mole) of N-dodecyl-4-hydroxy butyramide was dissolved in 193 grams of benzene and 6.3 grams of added pyridine.

To this mixture 10.4 grams (0.087 mole) of thionyl chloride in 27 grams of benzene was added slowly. The resulting mixture was then refluxed for 3 hours during which time hydrogen chloride and sulfur dioxide gases were evolved. Upon cessation of gas evolution, which marked completion of reaction, the reaction mixture was filtered and 20.4 grams of precipitated product was recovered and dried. The dried cake was analyzed for chlorine and found to contain 12.3% Cl (calculated Cl − 12.2% for $C_{16}H_{32}ClNO$). The solid product had a melting point of 53°-55° C. and was further subjected to spectral analysis. IR = 6.13 mu.

The bromo- or fluro- analog of the above product can be prepared by substituting thionyl bromide or thionyl fluoride in the above example.

EXAMPLE I

Preparation of N-decyl-4-(2-hydroxyethoxy) butyramide

In a steel autoclave, 243 grams (1 mole) of N-decyl-4-hydroxy-butyramide at a temperature of 130° C. was admixed with 44 grams (1 mole) of oxirane which was added to the autoclave as a compressed gas. The reaction mixture was stirred and autogenous pressure caused a drop in pressure during the reaction. After the reaction was complete in a period of about 2 hours, 281 grams of product were obtained. The product was then cooled to room temperature whereupon a light solid having a melting point of 48° C. was obtained. IR = 6.11 mu.

EXAMPLE J

Preparation of 2-[3-(decylcarbamoyl)propyloxy]ethylacetate

In a glass reaction vessel 17.7 grams (0.0616 mole) of N-decyl-4-(2-hydroxyethoxy)butyramide was admixed with 25.3 grams (0.25 mole) of acetic anhydride in the presence of 4 grams sodium acetate catalyst. This mixture was heated to 100° C. on a steam bath until a reaction was completed within a period of 3 hours. The mixture was then drowned in water, salted out and phase separated. The upper liquid phase was dried to 17.8 grams of liquid product having a refractive index $\eta_d^{25} = 1.4586$ and an IR of 6.09 mu.

EXAMPLE K

Preparation of 2-[3-(dodecylcarbamoyl)propyloxy]ethylchloroacetate

In a glass reaction vessel 10 grams (0.0318 mole) of N-dodecyl-4-(2-hydroxyethyl)butyramide, dissolved in 37.7 grams of benzene, was admixed with 3.6 grams (0.03180) of chloroacetyl chloride which had been added drop-wise to the benzene solution. The mixture was allowed to stand over night (for about 12 hours) and the reaction was completed. The contents of the reactor was then drowned in warm water, salted out and phase separated. The upper phase was then dried and yielded 9.0 grams of product which was a hard, waxy, off-white solid having a melting point of 58° C. and a chlorine analysis of 9.43% Cl (theoretical = 9.5% Cl for $C_{20}H_{38}ClNO_4$). Product IR = 6.13 mu.

Other N-alkyl carbamoyl alkoxy alkylhaloacetates or propanates or butyrates can be prepared by the method of this example by substituting the appropriate N-alkyl-4-(2-hydroxyalkyl) amide and halocarboxylic halide in the above example. For instance, N-decyl-4-(2-hydroxyethyl) butyramide and fluoroacetyl fluoride; N-dodecyl-4-(2-hydroxybutyl) pentamide and chlorobutyryl chloride; or N-tetradecyl-4-(2-hydroxyethyl)butyramide and bromopropionyl bromide, etc., can be substituted in Example K.

EXAMPLE L

Preparation of N-dodecyl-2(2-hydroxyethoxy) acetamide

In a glass reaction vessel 10.2 grams (0.1 mole) of 2-p-dioxanone was admixed with 18.5 grams (0.1 mole) of dodecyl amine and heated to 100° C. on a steam bath until reaction was completed within the period of 1 hour. The resulting liquid product was then poured on a glass plate and cooled to room temperature whereupon a pale yellow solid was formed. IR=6.06 mu.

Other N-alkyl hydroxyalkoxy acetamides, propionamides, or butyramides can be prepared by substituting the corresponding amine and/or lactone in the above example.

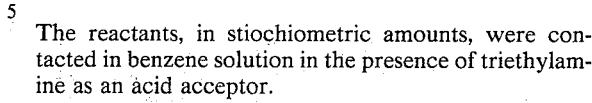

The reactants, in stiochiometric amounts, were contacted in benzene solution in the presence of triethylamine as an acid acceptor.

The reaction mixtures were stirred at 10° C. for 2 days after which the solid triethylamine hydrochloride was filtered off and the product was recovered by flash evaporation. The following fungicides were prepared in this manner:

| COMPOUND NO. | R' GROUP | IR IN mu | CHARACTERISTICS |
|---|---|---|---|
| V | $CH_3(CH_2)_{13}-$ | 6.10 | light solid; sol. in methanol |
| W | $CH_3(CH_2)_{15}-$ | 6.12 | light solid; sol. in acetone |
| X | $CH_3(CH_2)_9-$ | 6.13 | light solid; sol. in acetone & alcohol |
| Y | $CH_3(CH_2)_7-$ | 6.08 | light solid; sol. in alcohol, Cl calculated = 14.7%; found = 14.9% |

Additional hydroxyethoxybutyramide fungicides of the formula

ADDITIONAL FUNGICIDES PREPARED

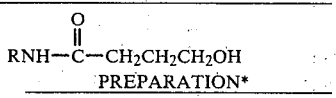

PREPARATION*

| COMPOUND NO. | R GROUP | REACTION TIME (hrs.) | REACTION (°C.) TEMPERATURE | CHARACTERISTICS |
|---|---|---|---|---|
| M | $CH_3(CH_2)_{13}-$ | 1 | 150 | white waxy solid IR = 6.06 mu |
| N | $CH_3(CH_2)_{15}-$ | 1 | 150 | white waxy solid |
| O | $CH_3(CH_2)_6-$ | 0.5 | 100 | white waxy solid IR = 6.12 mu |
| P | $CH_3(CH_2)_8-$ | 1 | 100 | white solid, soluble in methanol |
| Q | F-⟨⟩-CH₂- | 2 | 150 | m.p. 73–77° C. IR = 6.15 mu. |
| R | $(CH_3CH_2CH_2)CH-$ | 2 | 150 | tacky solid IR = 6.11 mu. |
| S | Cl-⟨⟩-CH₂- (Cl) | 0.5 | 100 | white solid, soluble in methanol |
| T | ⟨⟩-CH₂- (F) | 1 | 100 | white solid, soluble in ethanol |
| U | Cl-⟨⟩-CH₂- (Cl) | 1 | 100 | white solid, soluble in $C_{1-3}$ alcohols |

Additional chlorobutyramide fungicides of the formula

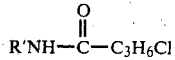

were prepared according to the general reaction

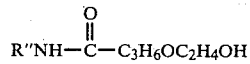

were prepared according to the general reaction

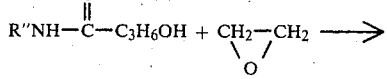

-continued

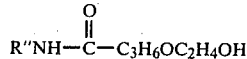

The hydroxy compound was melted and heated to 150° C. in the presence of 0.2% NaOH catalyst in an autoclave. Ethylene oxide was added incrementally to maintain a stiochiometeric ratio with the unreacted hydroxy compound. The product was separated, recovered and subjected to infrared analysis.

| COMPOUND NO. | R″ GROUP | IR IN mu |
|---|---|---|
| AA | $CH_3(CH_2)_6-$ | 6.10 |
| BB | $CH_3(CH_2)_{11}-$ | 6.12 |
| CC | $CH_3(CH_2)_{13}-$ | 6.13 |
| DD | $CH_3(CH_2)_{15}-$ | 6.12 |

Additional carbamoylpropyloxyethyl acetate fungicides were prepared according to the general reaction,

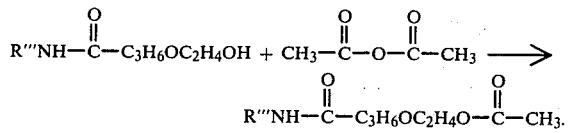

The reaction was carried out in a glass reactor with excess anhydride and in the presence of sodium acetate as a promotor, the mixture was heated on a steam bath for 4 hours with occasional stirring; after which the product mixture was drowned in ice water and product was precipitated. The product precipitate was washed with water, dried and subjected to IR analysis. The following compounds were prepared in this manner:

| COMPOUND NO. | R‴ GROUP | IR IN mu |
|---|---|---|
| EE | $CH_3(CH_2)_{11}-$ | 6.13 |
| FF | $CH_3(CH_2)_{15}-$ | 6.13 |
| GG | $CH_3(CH_2)_{13}-$ | 6.12 |

Additional carbamoylpropyloxyethyl chloroacetate fungicides were prepared according to the general reaction:

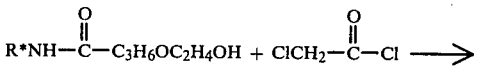

-continued

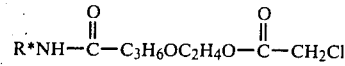

and the general procedure given in Example K. The following compounds were prepared in this manner:

| COMPOUND NO. | R*GROUP | IR IN mu |
|---|---|---|
| HH | $CH_3(CH_2)_9-$ | 6.10 |
| II | $CH_3(CH_2)_6-$ | 6.09 |
| JJ | $CH_3(CH_2)_{13}-$ | 6.14 |
| KK | $CH_3(CH_2)_{15}-$ | 6.13 |

Additional hydroxyethoxy acetamide fungicides were prepared according to the following general formula

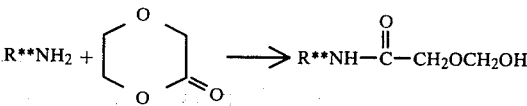

Stiochiometric amounts of the amine reactant and frozen dioxanone were melted and introduced into a glass reactor. The mixture was stirred and maintained at 100° C. for a period of 2 hours after which heating was discontinued. The product when cool froze from the melt to a hard white solid, soluble in acetone. Products prepared by this method are the following:

| COMPOUND NO. | R** GROUP | IR IN mu |
|---|---|---|
| LL | $CH_3(CH_2)_7-$ | 6.07 |
| MM | $CH_3(CH_2)_{13}-$ | 6.06 |
| NN | $CH_3(CH_2)_7CH=CH(CH_2)_8-$ | 6.09 |
| OO | 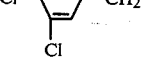 | 6.06 |

APPLICATION OF THE PRESENT FUNGICIDES TO PHANEROGAMIA PLANTS FOR CONTROL OF EUMYCOTINA FUNGI

The above fungicides were applied to the plants for the control of fungi infections and the results indicated in the following Table II.

In Table II the fungicide tested is referred to by letter corresponding to the above examples. The plants, fungi and any commercial fungicide used as a control is referred to by number identifying those species in the following listings in Table I.

TABLE I

| PLANT | CLASS | PATHOGEN SPECIES | COMMON NAME | COMMERCIAL FUNGICIDE |
|---|---|---|---|---|
| 1. Tomato (*Hycopersicon esculentum*) | Deuteromycete | 1. *Alternaria* | early blight | 1. Daconil [tetrachloroisophthalonitrile] |
| 2. String bean (Phaseolus) | Phycomycete | 2. *Phytophthora infestans* | late blight | 2. Benomyl [methyl-1-(butylcarbamoyl)-2-benzimidazole carbamate] |
|  | Ascomycete | 3. *Erysiphe polygoni* | powdery mildew |  |
| 3. Pinto bean (Phaseolus) | Basidiomycete | 4. *Uromyces phaseoli* | bean rust | 3. Dexon [p-dimethylaminobenzenediazo sodium sulfate] |
|  | Basidiomycete | 5. *Uredinale* | smut & rust |  |
| 4. Rice (*oryza sativa*) | Deuteromycete | 6. *Helminthosporium oryzae* | Brown rice spot | 4. Karathane [2,4-dinitro-6-octylphenyl-crotonate] |
| 5. Cotton seet (*Gossypium hirsutum*) | Phycomycete | 7. *Pythium ultimum* | damping off | 5. Maneb [Manganese ethyl bis (dithiocarbamate)] |
|  | Deuteromycete | 8. *Rhizoctonia solani* | black shank |  |

TABLE I-continued

| PLANT | CLASS | PATHOGEN SPECIES | COMMON NAME | COMMERCIAL FUNGICIDE |
|---|---|---|---|---|
| 6. Garden Pea seed (*Pisum sativum*) | Basidiomycete | 9. *Fusarium lycopersici* | wilt | |
| 7. Tobacco (*Nicotiana tobacum*) | Phycomycete | 10. *Thielaviopsis basicola* | brown root rot of tobacco | 6. Plantvax [2,3-dihydro-5-carboanilido-6-methyl-1,4-oxathiin-4,4-dioxide] |
| | Deuteromycete | 11. *Sclerotium rolfsii* | southern wilt | |
| 8. Potato (*Solanum tuberosum*) | Ascomycete | 12. Anthracnose | ulcerous lesion | 7. Terraclor [pentachloro-nitrobenzene] |
| 9. Black Mustard (*Brassica nigra*) | Basidiomycete | 13. *Puccinia graminis* | black stem rust of cereal | 8. Terrazole [5-ethoxy-3-trichloromethyl-1,2,4-thiadiazole] |
| | Basidiomycete | 14. *Puccinia rubigo-vera* | leaf rust of cereal | |
| 10. Cucumber (*Cucmis sativus*) | Basidiomycete | 15. *Puccinia sorghi* | corn rust | 9. Vitavax [5,6-dihydro-2-methyl-1,4-oxathiin-3-carboxanilide] |
| | Deuteromycete | 16. *Sclerotinia sclerotiorum* | leaf drop | |
| 11. Wheat (*triticum graminis*) | Deuteromycete | 17. *Phymatotrichum omnivorum* | root rot of cotton | 10. Arasan [tetramethyl-thiuram disulfide] |
| | Phycomycete | 18. *Phytophthora cactorum* | canker rot | |
| 12. Corn (*zea mays*) | Deuteromycete | 19. *Phyllachora cochliobolus* | rot of grasses | |
| 13. Rose (Rosa) | | 20. *Escherichia Pseudomonas tobaci* | tobacco mosaic | |
| 14. Peach tree (*amygdalus persica*) | | 21. *Scabies* | cucumber scab | |

A stock solution for applying and testing the above fungicides was prepared as a standard formulation by forming a solution of 1000 ppm. Triton X-155 (surfactant)[1] in acetone. The solution is then diluted with water in a ratio of 1:9 to obtain an aqueous solution of 10% acetone and 100 ppm surfactant. Subsequently, the solution was further diluted with varying amounts of water upon the addition of fungicide so as to maintain a constant ratio of surfactant at all dosage levels.
1. Nonionic alkylarylpolyether alcohol Tests have shown that the present fungicides are equally soluble in polar and nonpolar solvents, such as for example, ethanol, methanol, metal ethyl ketone, ethyl ketone, dimethyl formamide, xylene, toluene, benzene, etc. Therefore, it is to be understood that any of these solvents may be substituted for acetone in the above stock solution, if desired.

When it is desirable to apply the fungicide in heavier dosages it may be ground and mixed to a wet slurry in a mixture of Pyrax ABB[2] and Microcel[3] (9:1) in a tissue homogenizer or it may be impregnated on Pyrax ABB-Microcel and ball milled, wet or dry, or the fungicide admixture can be processed through a hand colloid mill. Alternatively, the fungicide may be mixed with talc, bentonite, or any of the conventional particulate dispersing agents and applied as a powder to the infected plant species.
2. A talc indigenous to North America
3. A precipitated hydrated silica The fungicidal preparation can be applied in pre-emergence (PreE) or post-emergence (PostE) stages depending upon the nature of the pathogen and the preference or needs of the user, and may be contacted with the plant several days prior to induced infection or after infection.

In commercial application it is also to be understood that the present fungicides can be used in combination with conventional fungicides, such as for example, Benomyl, Daconil, Dexon, Karathane, Maneb, Plantvax, Terraclor, Terrazole, Vitavax, etc. In many cases the present fungicides exert a synergistic effect on commercial fungicides when combined therewith for the control and elimination of the pathogen.

In each of the following examples reported in Table II, two flats seeded with a species of the respective mono- or di-cotyledonous plants was employed and the fungicide was applied as a liquid spray to saturation and run-off on the plant in the third or fourth foliate stage, except in those cases where the infection is pythium ultimum or rhizoctonia solani (fungi Nos. 7 and 8 respectively in Table I). In these cases the present fungicide and the control were separately sprayed on the soil where infection had been induced after planting.

All soil and growing media were sterilized prior to planting so that the effect of the fungicide on each of the individual pathogens could be determined without interfering effects from multiple infections. The efficacy of each fungicide was rated on a scale of from 0 to 10, which number, multiplied by 10 corresponds to the % control of the pathogen in that particular plant.

It is to be understood that, in general, fungicides possess degrees of efficacy which vary with respect to the particular plant and pathogen being tested. In the following table, the commercial fungicide believed to provide the best results for the particular plant and fungus was selected as the control and these results formed the basis of comparison for the present carboxylic amides under substantially the same test conditions, at the same rate of application and after the same number of days following infection. Although many of the following experiments show a higher response for the controls, it should be borne in mind that the control is specific to the test pathogen and may have little or no control of other fungus species. Thus, Dexon, which is particularly effective against mould, i.e. damping-off (No. 7 in Table I), has substantially no activity toward higher fungi infections such as for example, blight (No. 1) or the rusts (Nos. 4 and 15). The superiority of the present compounds is realized in their broad spectrum of fungicidal control, even though their degree of efficacy in certain instances may be less than that found for the specialized control fungicide.

TABLE II

| EX. NO. | AMIDE TESTED | PLANT | FUNGUS INFECTION | APPLICATION OF TEST AMIDE CONC. ppm | RATE lb./acre | EFFICACY OF TEST AMIDE RATING | DAYS AFTER INFECTION | CONTROL | CONC. ppm | EFFICACY RATING |
|---|---|---|---|---|---|---|---|---|---|---|
| 1 | A | 4 | 6 | 260 | 25 | 3 | 7 | 1 | 250 | 6.5 |
| 2 | A | 1 | 1 | 260 | 25 | 4 | 7 | 1 | 250 | 10 |
| 3 | B | 2 | 3 | 260 | 25 | 5 | 7 | 2 | 250 | 10 |
| 4 | B | 4 | 6 | 260 | 25 | 6 | 7 | 5 | 250 | 6.5 |
| 5 | B | 1 | 1 | 260 | 25 | 4 | 7 | 1 | 250 | 10 |
| 6 | C | 2 | 3 | 260 | 25 | 5 | 7 | 2 | 250 | 10 |
| 7 | C | 4 | 6 | 260 | 25 | 9.5 | 7 | 5 | 250 | 6.5 |
| 8 | C | 1 | 1 | 260 | 25 | 9 | 7 | 1 | 250 | 10 |
| 9 | C | 2 | 4 | 260 | 25 | 8 | 7 | 2 | 250 | 10 |
| 10 | C | 2 | 4 | 125 | 25 | 4 | 14 | 6 | 125 | 10 |
| 11 | C | 2 | 4 | 62 | 25 | 4 | 14 | 6 | 62 | 9 |
| 12 | C | 2 | 4 | 31 | 25 | 2.5 | 14 | 6 | 31 | 7.5 |
| 13 | C | 4 | 6 | 125 | 25 | 7.5 | 14 | 5 | 125 | 9 |
| 14 | C | 4 | 6 | 62 | 25 | 7 | 14 | 5 | 62 | 7.5 |
| 15 | C | 4 | 6 | 31 | 25 | 3.5 | 14 | 5 | 31 | 3 |
| 16 | C | 4 | 6 | 260 | 12.5 | 4 | 7 | 5 | 260 | 3 |
| 17 | C | 4 | 6 | 260 | 6.3 | 3 | 7 | 5 | 260 | 3 |
| 18 | C | 4 | 6 | 260 | 3.2 | 4 | 7 | 5 | 260 | 4 |
| 19 | C | 1 | 1 | 125 | 25 | 7.5 | 14 | 5 | 125 | 10 |
| 20 | C | 1 | 1 | 62 | 25 | 5 | 14 | 5 | 62 | 10 |
| 21 | C | 1 | 1 | 31 | 25 | 2.5 | 14 | 5 | 31 | 9 |
| 22 | D | 2 | 3 | 260 | 25 | 4 | 14 | 2 | 250 | 10 |
| 23 | D | 4 | 6 | 260 | 25 | 7 | 14 | 1 | 250 | 6.5 |
| 24 | D | 1 | 1 | 260 | 25 | 8 | 14 | 1 | 250 | 10 |
| 25 | D | 4 | 6 | 260 | 25 | 10 | 14 | 6 | 250 | 10 |
| 26 | D | 2 | 4 | 125 | 25 | 9.5 | 7 | 6 | 125 | 10 |
| 27 | D | 2 | 4 | 62 | 25 | 9 | 7 | 6 | 62 | 9 |
| 28 | D | 2 | 4 | 31 | 25 | 8 | 7 | 6 | 31 | 7.5 |
| 29 | D | 4 | 6 | 125 | 25 | 6.5 | 7 | 5 | 125 | 9 |
| 30 | D | 4 | 6 | 62 | 25 | 4 | 7 | 5 | 62 | 7 |
| 31 | D | 4 | 6 | 31 | 25 | 3 | 7 | 5 | 31 | 5 |
| 32 | D | 4 | 6 | 260 | 12.5 | 5 | 7 | — | — | — |
| 33 | D | 4 | 6 | 260 | 6.3 | 4 | 7 | — | — | — |
| 34 | D | 4 | 6 | 260 | 3.2 | 4 | 7 | — | — | — |
| 35 | D | 1 | 1 | 125 | 25 | 9 | 7 | 5 | 125 | 10 |
| 36 | D | 1 | 1 | 62 | 25 | 8 | 7 | 5 | 62 | 10 |
| 37 | D | 1 | 1 | 31 | 25 | 5 | 7 | 5 | 31 | 9 |
| 38 | D | 12 | 15 | 260 | 25 | 9.9 | 7 | 6 | 260 | 10 |
| 39 | D | 12 | 15 | 130 | 25 | 7.8 | 7 | 6 | 130 | 9.7 |
| 40 | D | 12 | 15 | 65 | 25 | 5.5 | 7 | 6 | 65 | 8.8 |
| 41 | D | 12 | 15 | 125 | 25 | 9.4 | 7 | 6 | 125 | 9.8 |
| 42 | D | 12 | 15 | 62 | 25 | 8.5 | 7 | 6 | 62 | 9.3 |
| 43 | D | 12 | 15 | 31 | 25 | 8.1 | 7 | 6 | 31 | 8.7 |
| 44 | D | 1 | 2 | 300 | 25 | 9.8 | 7 | 1 | 300 | 10 |
| 45 | D | 1 | 2 | 100 | 25 | 9.5 | 7 | 1 | 100 | 9.9 |
| 46 | D | 1 | 2 | 33 | 25 | 8.3 | 7 | 1 | 33 | 9.9 |
| 47 | D | 1 | 2 | 17 | 25 | 4.4 | 7 | 1 | 17 | 9.9 |
| 48 | D | 12 | 15 | 62 | 25 | 8.8 | 7 | 6 | 62 | 9.7 |
| 49 | D | 12 | 15 | 31 | 25 | 7.1 | 7 | 6 | 31 | 8.3 |
| 50 | D | 12 | 15 | 15 | 25 | 5.0 | 7 | 6 | 15 | 6.5 |
| 51 | D | 1 | 2 | 125 | 25 | 8.6 | 7 | 5 | 125 | 10 |
| 52 | D | 1 | 2 | 62 | 25 | 3.5 | 7 | 5 | 62 | 10 |
| 53 | D | 1 | 2 | 31 | 25 | 3.1 | 7 | 5 | 31 | 9.6 |
| 54 | E | 4 | 6 | 250 | 11 | 2 | 14 | 1 | 250 | 10 |
| 55 | E | 1 | 1 | 250 | 11 | 7 | 14 | 1 | 250 | 10 |
| 56 | E | 4 | 6 | 125 | 25 | 3 | 7 | 1 | 125 | 7 |
| 57 | E | 4 | 6 | 62 | 25 | 2 | 7 | 1 | 62 | 5 |
| 58 | E | 4 | 6 | 31 | 25 | 2 | 7 | 1 | 31 | 4 |
| 59 | E | 1 | 1 | 125 | 25 | 5 | 7 | 1 | 125 | 9.1 |
| 60 | E | 1 | 1 | 62 | 25 | 5 | 7 | 1 | 62 | 9.1 |
| 61 | E | 1 | 1 | 31 | 25 | 4 | 7 | 1 | 31 | 9 |
| 62 | E | 1 | 1 | 125 | 25 | 2 | 7 | 5 | 125 | 8.5 |
| 63 | F | 2 | 2 | 260 | 25 | 3.5 | 14 | 1 | 250 | 10 |
| 64 | F | 4 | 6 | 260 | 25 | 9.5 | 14 | 1 | 250 | 10 |
| 65 | F | 1 | 1 | 260 | 25 | 6 | 14 | 1 | 250 | 7.5 |
| 66 | F | 2 | 4 | 125 | 25 | 9 | 7 | 6 | 125 | 10 |
| 67 | F | 2 | 4 | 62 | 25 | 8.5 | 7 | 6 | 62 | 10 |
| 68 | F | 2 | 4 | 31 | 25 | 7.5 | 7 | 6 | 31 | 9.1 |
| 69 | F | 2 | 4 | 260 | 6.3 | 3 | 7 | 6 | 250 | 10 |
| 70 | G | 4 | 6 | 260 | 25 | 4 | 7 | 1 | 250 | 6.5 |
| 71 | G | 1 | 1 | 260 | 25 | 5 | 7 | 5 | 250 | 10 |
| 72 | H | 2 | 3 | 260 | 25 | 10 | 14 | 2 | 250 | 10 |
| 73 | H | 2 | 4 | 260 | 25 | 9 | 14 | 6 | 250 | 9.1 |
| 74 | H | 4 | 6 | 260 | 25 | 7.5 | 7 | 1 | 250 | 7.5 |
| 75 | H | 2 | 4 | 260 | 12.5 | 5 | 7 | 6 | 250 | 10 |
| 76 | H | 2 | 4 | 260 | 6.3 | 5 | 7 | 6 | 250 | 10 |
| 77 | H | 2 | 4 | 260 | 3.2 | 6.5 | 7 | 6 | 260 | 10 |
| 78 | H | 2 | 4 | 125 | 25 | 9 | 7 | 6 | 125 | 10 |

TABLE II-continued

| EX. NO. | AMIDE TESTED | PLANT | FUNGUS INFECTION | APPLICATION OF TEST AMIDE CONC. ppm | RATE lb./acre | EFFICACY OF TEST AMIDE RATING | DAYS AFTER INFECTION | CONTROL | CONC. ppm | EFFICACY RATING |
|---|---|---|---|---|---|---|---|---|---|---|
| 79 | H | 2 | 4 | 62 | 25 | 7 | 7 | 6 | 62 | 10 |
| 80 | H | 2 | 4 | 31 | 25 | 7.5 | 7 | 6 | 31 | 9.1 |
| 81 | H | 4 | 6 | 260 | 12.5 | 3 | 7 | — | — | — |
| 82 | H | 4 | 6 | 260 | 6.3 | 3 | 7 | — | — | — |
| 83 | H | 4 | 6 | 260 | 3.2 | 3 | 7 | — | — | — |
| 84 | H | 4 | 6 | 125 | 25 | 4.5 | 7 | 1 | 125 | 9.1 |
| 85 | H | 4 | 6 | 62 | 25 | 3 | 7 | 1 | 62 | 8.5 |
| 86 | H | 4 | 6 | 31 | 25 | 3 | 7 | 1 | 31 | 4.5 |
| 87 | A | 6 | 7 | 260 | 50 | 3.5 | 7 | 3 | 260 | 6.5* |
| 88 | E | 5 | 8 | 260 | 50 | 1.5 | 7 | 9 | 260 | 7.5* |
| 89 | G | 6 | 7 | 260 | 50 | 8 | 7 | 3 | 260 | 6.5* |
| 90 | I | 2 | 3 | 260 | 25 | 6 | 14 | 2 | 250 | 9.1 |
| 91 | I | 4 | 6 | 260 | 25 | 10 | 14 | 1 | 250 | 9 |
| 92 | I | 5 | 8 | 260 | 50 | 3 | 7 | 9 | 250 | 9* |
| 93 | I | 4 | 6 | 260 | 12.5 | 4 | 7 | — | — | — |
| 94 | I | 4 | 6 | 260 | 6.3 | 5 | 7 | — | — | — |
| 95 | I | 4 | 6 | 260 | 3.2 | 4.5 | 7 | — | — | — |
| 96 | I | 4 | 6 | 125 | 25 | 6 | 7 | 2 | 125 | 8 |
| 97 | I | 4 | 6 | 62 | 25 | 3.5 | 7 | 6 | 62 | 7 |
| 98 | I | 4 | 6 | 31 | 25 | 4 | 7 | 1 | 31 | 6.5 |
| 99 | J | 4 | 6 | 125 | 25 | 8 | 7 | 1 | 125 | 10 |
| 100 | J | 4 | 6 | 62 | 25 | 6 | 7 | 1 | 62 | 9.1 |
| 101 | J | 4 | 6 | 31 | 25 | 3.5 | 7 | 1 | 31 | 8 |
| 102 | J | 4 | 6 | 260 | 25 | 3.5 | 7 | — | — | — |
| 103 | J | 4 | 6 | 260 | 12.5 | 3.5 | 7 | — | — | — |
| 104 | J | 4 | 6 | 260 | 6.3 | 3.5 | 7 | — | — | — |
| 105 | K | 2 | 6 | 260 | 3.2 | 5 | 14 | 2 | 250 | 10 |
| 106 | K | 2 | 4 | 260 | 25 | 8 | 14 | 6 | 250 | 8.5 |
| 107 | K | 4 | 6 | 260 | 25 | 6 | 14 | 1 | 250 | 9 |
| 108 | L | 2 | 3 | 260 | 25 | 8.5 | 14 | 2 | 250 | 10 |
| 109 | L | 2 | 4 | 260 | 25 | 9.1 | 14 | 6 | 250 | 9 |
| 110 | L | 4 | 6 | 260 | 25 | 9.1 | 14 | 1 | 250 | 9.1 |
| 111 | L | 6 | 7 | 260 | 50 | 9.1 | 7 | 3 | 250 | 10 |
| 112 | L | 5 | 8 | 250 | 50 | 7 | 7 | 9 | 250 | 8.5* |
| 113 | L | 2 | 3 | 125 | 25 | 7.5/7 | 5/14 | 4 | 125 | 10/7;10/14 |
| 114 | L | 2 | 3 | 62 | 25 | 3.5/7 | 1.5/14 | 4 | 62 | 10/7;9.1/14 |
| 115 | L | 2 | 3 | 31 | 25 | 2.5 | 7 | 4 | 31 | 10 |
| 116 | L | 2 | 4 | 125 | 25 | 4 | 7 | 9 | 125 | 10 |
| 117 | L | 2 | 4 | 62 | 25 | 4 | 7 | 9 | 62 | 9 |
| 118 | L | 2 | 4 | 31 | 25 | 5.5 | 7 | 9 | 31 | 9 |
| 119 | L | 2 | 4 | 250 | 12.5 | 5.5 | 7 | — | — | — |
| 120 | L | 2 | 4 | 250 | 6.3 | 3 | 7 | 9 | 250 | 10 |
| 121 | L | 2 | 4 | 250 | 3.2 | 4.5 | 7 | 9 | 250 | 7.5 |
| 122 | L | 2 | 4 | 250 | 1.6 | | 7 | 9 | 250 | 6 |
| 123 | L | 4 | 6 | 125 | 25 | 4 | 7 | 1 | 125 | 9.1 |
| 124 | L | 4 | 6 | 62 | 25 | 2 | 7 | 1 | 62 | 9.1 |
| 125 | L | 4 | 6 | 31 | 25 | 3.5 | 7 | 1 | 31 | 8 |
| 126 | L | 4 | 6 | 250 | 12.5 | 4 | 7 | — | — | — |
| 127 | L | 4 | 6 | 250 | 6.3 | 3 | 7 | — | — | — |
| 128 | L | 4 | 6 | 250 | 3.2 | 3 | 7 | — | — | — |
| 129 | M | 2 | 6 | 250 | 11 | 9 | 14 | 6 | 250 | 10 |
| 130 | M | 4 | 1 | 250 | 11 | 3 | 14 | 1 | 250 | 10 |
| 131 | M | 2 | 6 | 250 | 11 | 2 | 7 | 6 | 250 | 10 |
| 132 | M | 2 | 6 | 250 | 11 | 2 | 7 | 6 | 250 | 10 |
| 133 | M | 2 | 6 | 250 | 5.5 | 3.5 | 7 | 6 | 250 | 10 |
| 134 | M | 2 | 6 | 250 | 2.7 | 2.5 | 7 | 6 | 250 | 10 |
| 135 | M | 2 | 6 | 125 | 25 | 9.1 | 7 | 6 | 125 | 10 |
| 136 | M | 2 | 6 | 62 | 25 | 9.1 | 7 | 6 | 62 | 9.5 |
| 137 | M | 2 | 6 | 31 | 25 | 9.1 | 7 | 6 | 31 | 8.5 |
| 138 | M | 2 | 6 | 15 | 25 | 7 | 7 | 6 | 15 | 7.5 |
| 139 | M | 2 | 6 | 260 | 25 | 4 | 7 | 6 | 260 | 9.1 |
| 140 | N | 2 | 6 | 250 | 11 | 9 | 14 | 6 | 250 | 10 |
| 141 | N | 4 | 1 | 250 | 11 | 4 | 14 | 1 | 250 | 10 |
| 142 | N | 2 | 6 | 62 | 25 | 9 | 7 | 6 | 62 | 9 |
| 143 | N | 2 | 6 | 31 | 25 | 7 | 7 | 6 | 31 | 8 |
| 144 | N | 2 | 6 | 15 | 25 | 5.5 | 7 | 6 | 15 | 7 |
| 145 | N | 1 | 1 | 125 | 25 | 2 | 7 | 5 | 125 | 8.5 |
| 146 | N | 1 | 1 | 62 | 25 | 2.5 | 7 | 5 | 62 | 5 |
| 147 | N | 12 | 15 | 260 | 25 | 7 | 14 | 6 | 260 | 10 |
| 148 | N | 12 | 15 | 130 | 25 | 7.2 | 14 | 6 | 130 | 9.7 |
| 149 | N | 12 | 15 | 65 | 25 | 5 | 14 | 6 | 65 | 8.8 |
| 150 | N | 2 | 4 | 260 | 25 | 3 | 14 | 6 | 260 | 9.1 |
| 151 | N | 12 | 15 | 260 | 25 | 8.2 | 7 | 6 | 260 | 10 |
| 152 | N | 12 | 15 | 62 | 25 | 6 | 7 | 6 | 62 | 5 |
| 153 | N | 12 | 15 | 15 | 25 | 5 | 7 | 6 | 15 | 4.5 |
| 154 | N | 2 | 6 | 125 | 25 | 7 | 7 | 6 | 125 | 10 |
| 155 | N | 2 | 6 | 62 | 25 | 8 | 7 | 6 | 62 | 9 |
| 156 | N | 2 | 6 | 31 | 25 | 7 | 7 | 6 | 31 | 8.5 |

TABLE II-continued

| EX. NO. | AMIDE TESTED | PLANT | FUNGUS INFECTION | APPLICATION OF TEST AMIDE CONC. ppm | RATE lb./acre | EFFICACY OF TEST AMIDE RATING | DAYS AFTER INFECTION | CONTROL | CONC. ppm | EFFICACY RATING |
|---|---|---|---|---|---|---|---|---|---|---|
| 157 | N | 2 | 6 | 250 | 11 | 3 | 7 | 6 | 250 | 10 |
| 158 | N | 2 | 6 | 250 | 5.5 | 2 | 7 | 6 | 250 | 10 |
| 159 | N | 2 | 6 | 250 | 2.7 | 2.5 | 7 | 6 | 250 | 10 |
| 160 | O | 4 | 6 | 260 | 25 | 4 | 14 | 1 | 250 | 9 |
| 161 | O | 1 | 1 | 260 | 25 | 5 | 14 | 1 | 250 | 9.1 |
| 162 | P | 4 | 6 | 260 | 25 | 5 | 14 | 1 | 250 | 9 |
| 163 | P | 1 | 1 | 260 | 25 | 3 | 14 | 1 | 250 | 9.1 |
| 164 | Q | 4 | 6 | 260 | 25 | 4 | 14 | 1 | 250 | 9 |
| 165 | Q | 1 | 1 | 260 | 25 | 7 | 14 | 1 | 250 | 9.1 |
| 166 | Q | 1 | 1 | 62 | 25 | 4.5 | 7 | 5 | 62 | 7.5 |
| 167 | Q | 1 | 1 | 31 | 25 | 2.5 | 7 | 5 | 31 | 4 |
| 168 | R | 2 | 4 | 260 | 25 | 3 | 14 | 6 | 250 | 10 |
| 169 | R | 4 | 6 | 260 | 25 | 4 | 14 | 1 | 250 | 9.1 |
| 170 | S | 2 | 4 | 260 | 25 | 5.5 | 14 | 6 | 250 | 10 |
| 171 | S | 4 | 6 | 260 | 25 | 4 | 14 | 1 | 250 | 8.5 |
| 172 | T | 2 | 4 | 260 | 25 | 8 | 14 | 6 | 250 | 10 |
| 173 |   | 4 | 6 | 260 | 25 | 3 | 14 | 1 | 250 | 8.5 |
| 174 | U | 4 | 6 | 260 | 25 | 3 | 14 | 1 | 250 | 9 |
| 175 | V | 2 | 3 | 260 | 25 | 6.5 | 14 | 2 | 250 | 10 |
| 176 | V | 2 | 4 | 260 | 25 | 3 | 14 | 6 | 250 | 9.1 |
| 177 | V | 4 | 6 | 260 | 25 | 4 | 14 | 1 | 250 | 7.5 |
| 178 | W | 2 | 3 | 260 | 25 | 2 | 7 | 2 | 250 | 10 |
| 179 | W | 2 | 4 | 260 | 25 | 3 | 7 | 6 | 250 | 9.1 |
| 180 | W | 4 | 6 | 260 | 25 | 4 | 7 | 1 | 250 | 7.5 |
| 181 | X | 4 | 6 | 260 | 25 | 9.1 | 7 | 1 | 250 | 7.5 |
| 182 | X | 4 | 6 | 125 | 25 | 3 | 7 | 1 | 125 | 9.1 |
| 183 | X | 4 | 6 | 62 | 25 | 3 | 7 | 1 | 62 | 8.5 |
| 184 | X | 4 | 6 | 31 | 25 | 3 | 7 | 1 | 31 | 4.5 |
| 185 | X | 4 | 6 | 260 | 12.5 | 3 | 7 | — | — | — |
| 186 | X | 4 | 6 | 260 | 6.3 | 3 | 7 | — | — | — |
| 187 | X | 4 | 6 | 260 | 3.2 | 3 | 7 | — | — | — |
| 188 | Y | 2 | 3 | 260 | 25 | 9 | 14 | 2 | 250 | 10 |
| 189 | Y | 4 | 6 | 260 | 25 | 3.5 | 14 | 1 | 250 | 7.5 |
| 190 | AA | 4 | 6 | 260 | 25 | 4 | 14 | 1 | 250 | 9 |
| 191 | AA | 5 | 8 | 260 | 50 | 2 | 7 | 9 | 250 | 9* |
| 192 | BB | 2 | 3 | 260 | 25 | 8.1 | 14 | 2 | 250 | 10 |
| 193 | BB | 2 | 4 | 260 | 25 | 9.1 | 14 | 6 | 250 | 10 |
| 194 | BB | 4 | 6 | 260 | 25 | 8.5 | 14 | 1 | 250 | 8.5 |
| 195 | BB | 5 | 8 | 260 | 50 | 2 | 7 | 9 | 250 | 7.5* |
| 196 | BB | 4 | 6 | 125 | 25 | 4 | 7 | 1 | 125 | 10 |
| 197 | BB | 4 | 6 | 62 | 25 | 3 | 7 | 1 | 62 | 9.1 |
| 198 | BB | 4 | 6 | 31 | 25 | 3 | 7 | 1 | 31 | 8 |
| 199 | BB | 4 | 6 | 260 | 12.5 | 4 | 7 | — | — | — |
| 200 | BB | 4 | 6 | 260 | 6.3 | 4 | 7 | — | — | — |
| 201 | BB | 4 | 6 | 260 | 3.2 | 4 | 7 | — | — | — |
| 202 | BB | 2 | 4 | 125 | 25 | 6 | 7 | 9 | 125 | 10 |
| 203 | BB | 2 | 4 | 62 | 25 | 6 | 7 | 9 | 62 | 9 |
| 204 | BB | 2 | 4 | 31 | 25 | 6.5 | 7 | 9 | 31 | 9 |
| 205 | BB | 2 | 4 | 260 | 12.5 | 3 | 7 | 9 | 250 | 9 |
| 206 | BB | 2 | 4 | 260 | 6.3 | 3.5 | 7 | 9 | 250 | 10 |
| 207 | BB | 2 | 4 | 260 | 3.2 | 4 | 7 | 9 | 260 | 7.5 |
| 208 | CC | 2 | 3 | 260 | 25 | 5.2 | 14 | 2 | 250 | 10 |
| 209 | CC | 2 | 4 | 260 | 25 | 9.1 | 14 | 6 | 250 | 10 |
| 210 | CC | 4 | 6 | 260 | 25 | 9 | 14 | 1 | 250 | 8.5 |
| 211 | CC | 2 | 4 | 125 | 25 | 9 | 7 | 9 | 125 | 10 |
| 212 | CC | 2 | 4 | 62 | 25 | 9 | 7 | 9 | 62 | 9 |
| 213 | CC | 2 | 4 | 31 | 25 | 7.5 | 7 | 9 | 31 | 9 |
| 214 | CC | 2 | 4 | 260 | 12.5 | 4 | 7 | — | — | — |
| 215 | CC | 2 | 4 | 260 | 6.3 | 3 | 7 | 9 | 250 | 10 |
| 216 | CC | 2 | 4 | 260 | 3.2 | 3 | 7 | 9 | 250 | 7.5 |
| 217 | CC | 4 | 6 | 125 | 25 | 7.5 | 7 | 1 | 125 | 10 |
| 218 | CC | 4 | 6 | 62 | 25 | 3 | 7 | 1 | 62 | 9.1 |
| 219 | CC | 4 | 6 | 31 | 25 | 3 | 7 | 1 | 31 | 8 |
| 220 | CC | 4 | 6 | 260 | 12.5 | 5.5 | 7 | — | — | — |
| 221 | CC | 4 | 6 | 260 | 6.3 | 4.5 | 7 | — | — | — |
| 222 | CC | 4 | 6 | 260 | 3.2 | 5.2 | 7 | — | — | — |
| 223 | DD | 2 | 4 | 260 | 25 | 9 | 14 | 6 | 250 | 9.1 |
| 224 | DD | 4 | 6 | 260 | 25 | 4 | 14 | 1 | 250 | 9 |
| 225 | DD | 2 | 4 | 125 | 25 | 7.2 | 7 | 6 | 125 | 10 |
| 226 | DD | 2 | 4 | 62 | 25 | 8.2 | 7 | 6 | 62 | 9 |
| 227 | DD | 2 | 4 | 31 | 25 | 8.1 | 7 | 6 | 31 | 6.5 |
| 228 | DD | 2 | 4 | 260 | 6.3 | 3 | 7 | 6 | 250 | 2.1 |
| 229 | DD | 2 | 4 | 250 | 1.6 | 3.5 | 7 | 6 | 250 | 2.1 |
| 230 | DD | 2 | 4 | 250 | 25 | 3.5 | 14 | 6 | 250 | 10 |
| 231 | DD | 2 | 4 | 250 | 25 | 3.5 | 7 | 10 | 250 | 2.5 |
| 232 | DD | 2 | 4 | 50 | 25 | 3 | 14 | 6 | 50 | 6.5 |
| 233 | DD | 2 | 4 | 50 | 25 | 3 | 7 | 10 | 50 | 3 |
| 234 | DD | 3 | 4 | 250 | 25 | 7.5 | 7 | 6 | 250 | 10 |

TABLE II-continued

| EX. NO. | AMIDE TESTED | PLANT | FUNGUS INFECTION | APPLICATION OF TEST AMIDE | | EFFICACY OF TEST AMIDE | | CON-TROL | CONC. ppm | EFFICACY RATING |
|---|---|---|---|---|---|---|---|---|---|---|
| | | | | CONC. ppm | RATE lb./acre | RATING | DAYS AFTER INFECTION | | | |
| 235 | DD | 2 | 4 | 250 | 25 | 7.5 | 7 | 10 | 250 | 10 |
| 236 | DD | 2 | 4 | 50 | 25 | 8 | 7 | 6 | 50 | 7 |
| 237 | DD | 2 | 4 | 50 | 25 | 8 | 7 | 10 | 50 | 10 |
| 238 | DD | 12 | 15 | 125 | 25 | 6 | 7 | 6 | 125 | 10 |
| 239 | DD | 12 | 15 | 62 | 25 | 6 | 7 | — | — | — |
| 240 | DD | 12 | 15 | 31 | 25 | 6 | 7 | 6 | 31 | 10 |
| 241 | DD | 12 | 15 | 7 | 25 | 6 | 7 | 6 | 7 | 7 |
| 242 | EE | 2 | 4 | 260 | 25 | 9 | 14 | 6 | 250 | 10 |
| 243 | EE | 4 | 6 | 260 | 25 | 4 | 14 | 1 | 250 | 6.5 |
| 244 | FF | 2 | 4 | 260 | 25 | 7 | 14 | 6 | 250 | 9.1 |
| 245 | FF | 4 | 6 | 260 | 25 | 4 | 14 | 1 | 250 | 7 |
| 246 | GG | 2 | 3 | 260 | 25 | 4.5 | 7 | 2 | 250 | 10 |
| 247 | GG | 2 | 4 | 260 | 25 | 9.1 | 7 | 6 | 250 | 8.5 |
| 248 | GG | 4 | 6 | 260 | 25 | 3 | 7 | 1 | 250 | 9 |
| 249 | HH | 2 | 4 | 260 | 25 | 6.5 | 14 | 6 | 250 | 8.5 |
| 250 | HH | 4 | 6 | 260 | 25 | 7 | 14 | 1 | 250 | 9 |
| 251 | II | 2 | 4 | 260 | 25 | 5 | 14 | 6 | 250 | 8.5 |
| 252 | II | 4 | 6 | 260 | 25 | 6 | 14 | 1 | 250 | 9 |
| 253 | JJ | 2 | 3 | 260 | 25 | 3 | 14 | 2 | 250 | 10 |
| 254 | JJ | 3 | 4 | 260 | 25 | 8 | 14 | 6 | 250 | 8.5 |
| 255 | JJ | 4 | 6 | 260 | 25 | 8 | 14 | 1 | 250 | 9 |
| 256 | JJ | 2 | 4 | 125 | 25 | 10 | 7 | 9 | 125 | 10 |
| 257 | JJ | 2 | 4 | 62 | 25 | 9 | 7 | 9 | 62 | 9 |
| 258 | JJ | 2 | 4 | 31 | 25 | 7.5 | 7 | 9 | 31 | 9 |
| 259 | JJ | 2 | 4 | 250 | 12.5 | 4 | 7 | — | — | — |
| 260 | JJ | 2 | 4 | 250 | 6.3 | 5 | 7 | 9 | 250 | 10 |
| 261 | JJ | 2 | 4 | 250 | 3.2 | 4 | 7 | 9 | 250 | 7.5 |
| 262 | JJ | 2 | 4 | 250 | 1.6 | 4 | 7 | 9 | 250 | 6 |
| 263 | JJ | 2 | 4 | 250 | 25 | 3 | 7 | 6 | 250 | 10 |
| 264 | JJ | 2 | 4 | 50 | 25 | 3.5 | 7 | 6 | 250 | 6.5 |
| 265 | JJ | 2 | 4 | 250 | 25 | 8.5 | 7 | 6 | 250 | 10 |
| 266 | JJ | 2 | 4 | 50 | 25 | 6 | 7 | 6 | 250 | 7 |
| 267 | JJ | 4 | 6 | 125 | 25 | 5 | 7 | 1 | 125 | 10 |
| 268 | JJ | 4 | 6 | 62 | 25 | 3 | 7 | 1 | 62 | 10 |
| 269 | JJ | 4 | 6 | 31 | 25 | 3 | 7 | 1 | 31 | 8.5 |
| 270 | JJ | 4 | 6 | 250 | 12.5 | 4 | 7 | — | — | — |
| 271 | JJ | 4 | 6 | 250 | 6.3 | 3 | 7 | — | — | — |
| 272 | JJ | 4 | 6 | 250 | 3.2 | 3 | 7 | — | — | — |
| 273 | KK | 2 | 4 | 260 | 25 | 9 | 14 | 6 | 250 | 8.5 |
| 274 | KK | 4 | 6 | 260 | 25 | 5 | 14 | 1 | 250 | 9 |
| 275 | LL | 2 | 4 | 260 | 25 | 4.5 | 14 | 6 | 250 | 9 |
| 276 | LL | 4 | 6 | 260 | 25 | 5 | 14 | 1 | 250 | 9.1 |
| 277 | MM | 2 | 4 | 260 | 25 | 9.1 | 14 | 6 | 250 | 9 |
| 278 | MM | 4 | 6 | 260 | 25 | 9.1 | 14 | 1 | 250 | 9.1 |
| 279 | MM | 2 | 4 | 125 | 25 | 9 | 7 | 9 | 125 | 10 |
| 280 | MM | 2 | 4 | 62 | 25 | 9 | 7 | 9 | 62 | 9 |
| 281 | MM | 2 | 4 | 31 | 25 | 5.5 | 7 | 9 | 31 | 9 |
| 282 | MM | 2 | 4 | 260 | 12.5 | 5.5 | 7 | — | — | — |
| 283 | MM | 2 | 4 | 260 | 6.3 | 5.5 | 7 | 9 | 250 | 7.5 |
| 284 | MM | 2 | 4 | 260 | 3.2 | 5 | 7 | 9 | 250 | 7.5 |
| 285 | MM | 2 | 4 | 260 | 1.6 | 4 | 7 | 9 | 250 | 6 |
| 286 | MM | 4 | 7 | 125 | 25 | 4 | 7 | 1 | 125 | 9.1 |
| 287 | MM | 4 | 6 | 62 | 25 | 4 | 7 | 1 | 62 | 9.1 |
| 288 | MM | 4 | 6 | 31 | 25 | 4 | 7 | 1 | 31 | 8 |
| 289 | MM | 4 | 6 | 260 | 12.5 | 3 | 7 | — | — | — |
| 290 | MM | 4 | 6 | 260 | 6.3 | 3 | 7 | 1 | 260 | 10 |
| 291 | NN | 2 | 3 | 260 | 25 | 4 | 14 | 2 | 250 | 10 |
| 292 | NN | 2 | 4 | 260 | 25 | 9.1 | 14 | 6 | 250 | 9 |
| 293 | NN | 4 | 6 | 260 | 25 | 7 | 14 | 1 | 250 | 9.1 |
| 294 | NN | 2 | 4 | 125 | 25 | 7.5 | 7 | 6 | 125 | 10 |
| 295 | NN | 2 | 4 | 62 | 25 | 5.5 | 7 | 6 | 62 | 9 |
| 296 | NN | 2 | 4 | 31 | 25 | 4.5 | 7 | 6 | 31 | 9 |
| 297 | NN | 2 | 4 | 260 | 12.5 | 6 | 7 | — | — | — |
| 298 | NN | 2 | 4 | 260 | 6.3 | 6 | 7 | 6 | 250 | 10 |
| 299 | NN | 2 | 4 | 260 | 3.2 | 6 | 7 | 6 | 250 | 7.5 |
| 300 | NN | 2 | 4 | 260 | 1.6 | 6 | 7 | 6 | 250 | 6 |
| 301 | NN | 4 | 6 | 125 | 25 | 3.5 | 7 | 1 | 125 | 9.1 |
| 302 | NN | 4 | 6 | 62 | 25 | 2 | 7 | 1 | 62 | 9.1 |
| 303 | NN | 4 | 6 | 31 | 25 | 3 | 7 | 1 | 31 | 8 |
| 304 | NN | 4 | 6 | 260 | 12.5 | 2 | 7 | — | — | — |
| 305 | NN | 4 | 6 | 260 | 6.3 | 2 | 7 | — | — | — |
| 306 | NN | 4 | 6 | 260 | 3.2 | 2 | 7 | — | — | — |
| 307 | OO | 2 | 4 | 260 | 25 | 7 | 14 | 6 | 250 | 9 |
| 308 | OO | 4 | 6 | 260 | 25 | 3 | 14 | 1 | 250 | 9.1 |

*tested at 25 lb./acre

EXAMPLE 309

Of the above fungicides, compounds G, I and L are among the best of those tested for inhibition of destructive seed decay fungi, i. e. damping off and black shank pathogens (Nos. 7 and 8) on acid delinted cotton seed (plant No. 5) and pea seeds (plant No. 6). Specifically, testing of fungicides G, I and L is carried out by preparing a culture of Rhizoctonia solani and of Pythium ultimum, each in a sterile medium of corn meal and Zonolite in 4-inch Petri dishes. The Rhizoctonia solani is then blended with sterile soil in which the cotton seeds are planted. Pythium ultimum is similarly blended with sterile soil in a separate area where pea seeds have been planted. Each of the pathogen infected areas are divided into three separate portions and introduced into individual plastic containers for separately testing the fungicides G, I and L on each of the infected plant species.

A suspension at 2080 ppm of each fungicide is then applied to each of the six plastic containers at a rate of 10 ml/inch (equivalent to 50 lbs./acre). The treated seeds are closed in their respective containers for three days before opening and, after seven days are examined for emergence of the seedlings and freedom of hypocotyls from brown lesions. The test fungicides are rated upon % emergents and severity of lesions on survivors based on a scale of 0–10; 0 indicating severe infection on all plants and 10 indicating no lesions and complete elimination of the pathogen. Test fungicides G, I and L have ratings of 6 or better, which is regarded as adequate control. These test fungicides also provide more than 50% control of root rot (pathogen No. 17) of the emerged cotton plants when inoculated with this fungus.

EXAMPLE 310

Fungicides, D, G, I and L, and other species within the scope of this invention, can be employed against a wide assortment of soil inhabiting fungi, such as wilt (No. 9) of tomato (No. 1); brown root rot (No. 10) of tobacco (No. 7) and Southern wilt (No.11) of solanaceous crops (eg. No. 8) by following the general procedure of Example 309 in applying the fungicidal sprays. Fungicides D, G, I and L provide greater than 50% control of these pathogens.

EXAMPLE 311

The fungicides, D, G, I and L, as well as other species of this invention, are effective against
leaf rust (No. 14) and stem rust (No. 13) in wheat (No.11) smut (No. 5) in corn (No. 12) anthracnose (No. 12) in pinto beans (No. 3) scab (No. 21) in cucumber (No. 10) tobacco mosaic (No. 20) in tobacco (No. 7) mildew (No. 3) in black mustard (No. 9) leaf spot and canker (No. 18) in roses (No. 13) and leaf drop (No. 16) in peach trees (No. 14).
The respective plants are sprayed to run off with the fungicide in a concentration of from about 25 ppm to about 500 ppm, e.g. about 250 ppm in aqueous alcoholic solution. Since the present fungicides are nontoxic to plants, the treatment may be repeated as often as necessary or desired to control, eliminate or prevent fungus infection.

EXAMPLES 312 THROUGH 315

The following tests indicate the tolerance of crops for the present carboxylic amides and its residues and the effect of soil moisture and temperature on the fungicidal efficacy and persistance on the plant. The results are reported in the following Table III. In each case the plant, pathogen and fungicide tested are referred to by number corresponding to the species listed in Table I. In the third column, the concentration of the fungicide is reported in estimated lbs./acre and the remarks are based on the effect noted after the number of days following application of the fungicide.

TABLE III

| EXAMPLE | TEST SPECIES (plant-pathogen fungicide) | FUNGICIDE CONCENTRATION | DAYS AFTER APPLICATION | REMARKS |
|---|---|---|---|---|
| 312 | 12-15-DD | 12 lbs./acre | 7 | no phytotoxicity observed - foliar persistence |
| 313 | 1-2-D | 12 lbs./acre | 14 | no phytotoxicity observed - foliar persistence |
| 314 | 2-3-D | 25 lbs./acre | 14 | no phytotoxicity observed - foliar persistence |
| 315 | 4-6-H | 25 lbs./acre | 7 | no phytotoxicity observed - foliar persistence |

What is claimed is:

1. A process for the control of Eumycotina fungi which comprises applying to a plant a fungicidal amount of one or more amide fungicides having the formula:

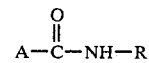

wherein A is hydroxyalkyl containing from 2 to 14 carbon atoms and is and wherein R is an organic radical of from 4 to 20 carbon atoms and is selected from the group consisting of an acyclic alkyl radical, an alkenyl radical having one or more doubly bonded carbon atoms and a mono on di-fluoxinated benzyl radical.

2. The process of claim 1 wherein the fungicide, in a concentration of from about 25 ppm. to about 2,500 ppm is applied in a liquid composition in an inert liquid carrier.

3. The process of claim 2 wherein the concentration of the fungicide in the carrier is between about 30 ppm and about 800 ppm.

4. The process of claim 1 wherein the fungicide in a concentration of from about 25 ppm to about 2,500 ppm is applied in an inert solid carrier.

5. The process of claim 4 wherein the concentration of the fungicide in the carrier is between about 30 ppm and about 800 ppm.

6. The process of claim 2 wherein the fungicidal composition is applied to the plant at a rate of between about 0.5 and about 30 pounds per acre.

7. The process of claim 6 wherein the fungicidal composition is applied to the plant at a rate of between about 1 and about 10 pounds per acre.

8. The process of claim 2 wherein the fungicidal composition is an aqueous emulsion and contains a nonaqueous solvent and an emulsifying agent.

9. The process of claim 2 wherein the fungicidal composition is a liquid dispersion in water.

10. The process of claim 1 wherein R of the amide contains from 8 to 18 carbon atoms.

* * * * *